US007280251B1

United States Patent
Holub (10) Patent No.: US 7,280,251 B1
(45) Date of Patent: Oct. 9, 2007

(54) SYSTEM AND METHOD FOR CALIBRATING COLOR PRINTERS

(75) Inventor: Richard A. Holub, Rochester, NY (US)

(73) Assignee: Rah Color Technologies, Rochester, NY (US)

( * ) Notice: Subject to any disclaimer, the term of this patent is extended or adjusted under 35 U.S.C. 154(b) by 308 days.

(21) Appl. No.: 10/880,075

(22) Filed: Jun. 29, 2004

Related U.S. Application Data (60) Continuation-in-part of application No. 10/209,431, filed on Jul. 31, 2002, now Pat. No. 7,075,643, which is a division of application No. 09/139,498, filed on Aug. 25, 1998, now Pat. No. 6,459,425, said application No. 10/880,075 is a continuation-in-part of application No. 10/040,664, filed on Jan. 7, 2002, now Pat. No. 6,995,870, which is a division of application No. 09/135,692, filed on Aug. 18, 1998, now Pat. No. 6,157,735, which is a continuation of application No. 08/606,883, filed on Feb. 26, 1996, now Pat. No. 6,043,909.

(60) Provisional application No. 60/056,947, filed on Aug. 25, 1997.

(51) Int. Cl.
*H04N 1/40* (2006.01)

(52) U.S. Cl. .............................. 358/1.9; 358/1.15

(58) Field of Classification Search ............ 358/1.9, 358/2.1, 1.15–1.16, 518–523, 504–505, 400, 358/500; 356/425
See application file for complete search history.

(56) References Cited

U.S. PATENT DOCUMENTS

| 5,185,673 | A | * | 2/1993 | Sobol ........................ 358/296 |
| 5,835,817 | A | | 11/1998 | Bullock et al. |
| 5,859,711 | A | | 1/1999 | Barry et al. |
| 6,035,103 | A | | 3/2000 | Zuber |
| 6,043,894 | A | * | 3/2000 | Van Aken et al. .......... 356/425 |
| 6,097,471 | A | | 8/2000 | Buhr et al. |
| 6,219,155 | B1 | | 4/2001 | Zuber |
| 6,246,790 | B1 | | 6/2001 | Huang et al. |
| 6,256,638 | B1 | | 7/2001 | Dougherty et al. |
| 6,271,937 | B1 | | 8/2001 | Zuber |
| 6,282,311 | B1 | | 8/2001 | McCarthy et al. |
| 6,282,312 | B1 | | 8/2001 | McCarthy et al. |
| 6,282,313 | B1 | | 8/2001 | McCarthy et al. |
| 6,285,784 | B1 | | 9/2001 | Spaulding et al. |
| 6,301,393 | B1 | | 10/2001 | Spaulding et al. |
| 6,310,626 | B1 | | 10/2001 | Walker et al. |

(Continued)

OTHER PUBLICATIONS

Imation Verifi Accurate Web Color: Technology White Paper, 2000.

(Continued)

*Primary Examiner*—Thomas D. Lee
*Assistant Examiner*—Stephen Brinich
(74) *Attorney, Agent, or Firm*—Kenneth J. Lukacher (57) ABSTRACT

A system and method for calibrating color printers, and related particularly to, a system and method for calibrating color printers over a network utilizing a profile server (representing a networkable computer server system) which provides color transformations in accordance with printer configurations having at least information read from consumable ink or toner cartridges for such printers. Such color transformations enable different color printers, or even the same color printer with different printer configurations, to render color consistently.

41 Claims, 5 Drawing Sheets

U.S. PATENT DOCUMENTS

| | | |
|---|---|---|
| 6,320,668 B1 | 11/2001 | Kim |
| 6,335,983 B1 | 1/2002 | McCarthy et al. |
| 6,337,922 B2 | 1/2002 | Kumada |
| 6,341,175 B1 | 1/2002 | Usami |
| 6,342,951 B1 | 1/2002 | Eschbach et al. |
| 6,351,621 B1 | 2/2002 | Richards et al. |
| 6,369,901 B1 | 4/2002 | Buhr et al. |
| 6,373,580 B1 | 4/2002 | Walker |
| 6,380,951 B1 | 4/2002 | Petchenkine et al. |
| 6,381,343 B1 | 4/2002 | Davis et al. |
| 6,388,674 B1 | 5/2002 | Ito et al. |
| 6,404,509 B1 | 6/2002 | Kuwata et al. |
| 6,414,690 B1 | 7/2002 | Balasubramanian et al. |
| 6,429,875 B1 | 8/2002 | Pettigrew et al. |
| 6,430,311 B1 | 8/2002 | Kumada |
| 6,430,312 B1 | 8/2002 | Huang et al. |
| 6,437,792 B1 | 8/2002 | Ito et al. |
| 6,459,436 B1 | 10/2002 | Kumada et al. |
| 6,459,860 B1 | 10/2002 | Childers |
| 6,477,335 B1 | 11/2002 | Surya et al. |
| 6,483,524 B1 | 11/2002 | Petchenkine et al. |
| 6,501,850 B2 | 12/2002 | Setchell, Jr. |
| 6,505,256 B1 | 1/2003 | York |
| 6,516,089 B1 | 2/2003 | McCann et al. |
| 6,522,313 B1 | 2/2003 | Cottone |
| 6,522,778 B1 | 2/2003 | Tamagawa |
| 6,525,721 B1 | 2/2003 | Thomas et al. |
| 6,539,867 B2 | 4/2003 | Lee |
| 6,549,652 B1 | 4/2003 | Persiantsev et al. |
| 6,549,653 B1 | 4/2003 | Osawa et al. |
| 6,549,732 B2 | 4/2003 | Yoshizaki et al. |
| 6,559,944 B1 * | 5/2003 | Van Aken et al. .......... 356/425 |
| 6,580,524 B1 | 6/2003 | Weichmann et al. |
| 6,603,879 B2 | 8/2003 | Haikin et al. |
| 6,606,165 B1 | 8/2003 | Barry et al. |
| 6,615,729 B2 | 9/2003 | Hauck et al. |
| 6,621,923 B1 | 9/2003 | Gennetten |
| 6,624,908 B1 | 9/2003 | Petchenkine et al. |
| 6,625,402 B2 | 9/2003 | Takemoto |
| 6,633,396 B1 | 10/2003 | Barry et al. |
| 6,636,326 B1 | 10/2003 | Zuber |
| 6,644,771 B1 | 11/2003 | Silverbrook |
| 6,654,491 B1 | 11/2003 | Hidaka |
| 6,654,567 B2 | 11/2003 | Karakama et al. |
| 6,704,442 B2 | 3/2004 | Haikin et al. |
| 6,722,281 B2 | 4/2004 | Yamamoto |
| 6,725,772 B2 | 4/2004 | Martinez et al. |
| 6,748,471 B1 | 6/2004 | Keeney et al. |
| 6,757,450 B1 | 6/2004 | Gershony et al. |
| 6,784,995 B2 | 8/2004 | Merle et al. |
| 6,788,305 B1 | 9/2004 | Ohga |
| 6,803,921 B1 | 10/2004 | Balasubramanian et al. |
| 2002/0063907 A1 | 5/2002 | Harrington |
| 2002/0080335 A1 | 6/2002 | Silverbrook |
| 2002/0085749 A1 | 7/2002 | Setchell, Jr. |
| 2002/0097409 A1 | 7/2002 | Wexler et al. |
| 2002/0140985 A1 | 10/2002 | Hudson |
| 2003/0007023 A1 | 1/2003 | Barclay et al. |
| 2003/0068185 A1 | 4/2003 | Silverbrook |
| 2003/0112419 A1 | 6/2003 | Silverbrook |
| 2003/0177930 A1 | 9/2003 | Derhak et al. |
| 2004/0004651 A1 | 1/2004 | Silverbrook |
| 2004/0008327 A1 | 1/2004 | Silverbrook |

OTHER PUBLICATIONS

Radius PressView System User's Manual, Jun. 1995.
Radius PressView 17SR and PressView 21SR User's Manual, Mar. 1995.
Radius ProSense Display Calibrator User's Manual, Jun. 1995.

* cited by examiner

SYSTEM AND METHOD FOR CALIBRATING COLOR PRINTERS

This application is a continuation-in-part of U.S. patent application Ser. No. 10/209,431, filed Jul. 31, 2002 now U.S. Pat. No. 7,075,643, which is a divisional of U.S. patent application Ser. No. 09/139,498, filed Aug. 25, 1998, now U.S. Pat. No. 6,459,425, issued Oct. 1, 2002, claiming priority to U.S. Provisional Application No. 60/056,947, filed Aug. 25, 1997, and this application is a continuation-in-part of U.S. patent application Ser. No. 10/040,664, filed Jan. 7, 2002 now U.S. Pat. No. 6,995,870, which is a divisional of U.S. patent application Ser. No. 09/135,692, filed Aug. 18, 1998, now U.S. Pat. No. 6,157,735, filed Dec. 5, 2000, which is a continuation of U.S. patent application Ser. No. 08/606,883, filed Feb. 26, 1996, now U.S. Pat. No. 6,043,909, issued Mar. 28, 2000. The above-patent applications are herein incorporated by reference.

FIELD OF THE INVENTION

The present invention relates to system and method for calibrating color printers, and related particularly to, a system and method for calibrating color printers over a network utilizing a profile server (representing a network-able computer server system) which provides color transformations in accordance with printer configurations having at least information read from consumable ink or toner cartridges for such printers. Such color transformations enable different color printers, or even the same color printer with different printer configurations, to render color consistently. This is especially useful for high end printers used by publishers and printing houses for proofing or printing color in newspapers, periodicals, catalogs, marketing collateral, and the like. The present invention further relates to a cartridge having identifying information for the toner or ink in such cartridge used in providing transformations for calibration the color rendered by printers.

BACKGROUND OF THE INVENTION

U.S. Pat. Nos. 6,157,735, and 6,043,909 describe systems and methods for distributing and controlling color reproduction at multiple sites, and U.S. Pat. No. 6,459,425 describes a related system for automatic color calibration. In these patents, information is communicated for color matching at and among nodes of a network. A computer system called a profile server, is described in U.S. Pat. No. 6,459,425 for assisting a node in determining color calibration for color rendering device in response to color calibration data measured by a color calibration instrument at the rendering device. These patents also describe the import/export of generic and/or standardized color transformations. These transformations may be used in combination with linearization functions customized to a particular, nodal rendering device that are updated regularly. Where color matching among devices in a network is desired, these patents also describe the sharing of information, such as gamut data, to enable matching. In the case of video displays, U.S. Pat. No. 6,459,425 describes the use of multidimensional transformations that are based on measurements made at the time of manufacture of the display and provided in ROM, on diskette or over the Internet. After manufacture, simpler linearization and white balance calibration may be used to maintain the device in a known, baseline state. It would also be useful for hard copy rendering devices, such as color printers, to provide information about their configuration that would allow a user of color printer to obtain calibration data that could be used to prepared a color transformation adequate to handle at least the color-mixing part of device modeling.

SUMMARY OF THE INVENTION

It is the principal object of the present invention to provide a system and method for calibrating color printers based on printer configuration information including at least information read from a toner or ink cartridge at the color printer.

It is another object of the present invention to provide a system and method for calibration of a color printer in which a profile server operates responsive to received printer configuration information and/or color calibration data measured at the rendering device to provide color transformation and/or linearization curves for use by the printer.

It is another object of the present invention to provide toner or ink cartridges having stored information readable by one of the printer or user for use in calibrating color printers that use such cartridges.

Briefly described, the system has a network having multiple nodes in which one node has a profile server representing a computer system having a memory storage unit for a database, and one or more other of the nodes have a nodal computer system or device coupled to at least one color printer in which the nodes communicate between others of the nodes over the network. The database stores color profile data for controlling color reproduction by the different printers for different printer configurations. The profile server, via the network, receives data from the nodal computer system representing the printer configuration having at least the identifying information stored in a replaceable cartridge installable in the rendering device. In response to such received data, the profile server determines a color transformation (and/or linearization curves) useable by the printer, and sends such color transformation to the nodal computer system (or to the printer if no computer system is present at the node) for use when rendering color by the color printer.

The profile server responds to received printer configuration information and sends the color transformation to the requested node if stored in the database for the particular printer configuration, otherwise the color transformation is calculated as described in incorporated U.S. Pat. Nos. 6,459,425, 6,157,735, and 6,043,909.

The printer configuration data sent by a node to the profile server may further include user preferences for rendering on the rendering device to be included in the color transformation determined by the profile server.

Once received by the nodal computer system, linearization, gamuts, or other color rendering issues may be handled further at the node, as desired by the user, in which the color transformation received provides a base line in common color rendering by different color cartridges in the same rendering device upon which the user may then adjust as desired. Thus, different color rendering devices may render color in substantially the same manner as attainable by the devices by the use of color transformation received from the profile server in accordance with data read from a cartridge.

Typical hardcopy rendering devices are microprocessor-based systems for controlling their print rendering from toner or ink from installed cartridge(s). In the rendering device, a reader coupled to the microprocessor may be provided which is aligned (or in proximity to) the installed cartridge to read data defining the state of calibration of the cartridge and provide such read to data to the nodal computer system. Devices on or in a ink or toner cartridge for storing such data, such as an identifier (or code), may be passive or active Radio Frequency (RF) Identification Devices, barcodes, or non-volatile memory provided by wire or wirelessly. Alternatively, a software application may be provided which enables the user to input an identifier(s) from the cartridge or its packaging to a software application operating at a nodal computer system as input data, via keyboard and/or mouse, which may be transmitted to the profile server.

Data read by an input device or the user for a set of cartridges is sent to the profile server where the database is maintained and multidimensional transformations are prepared and stored. These transformations optimize performance at the level of the nodal system to printer interactions, where nodal system includes the nodal computer and its software applications, virtual proofing, and the like.

BRIEF DESCRIPTION OF THE DRAWINGS

The foregoing objects, features and advantages of the invention will become more apparent from a reading of the following description in connection with the accompanying drawings, in which.

DETAILED DESCRIPTION OF THE INVENTION

Figure 1:
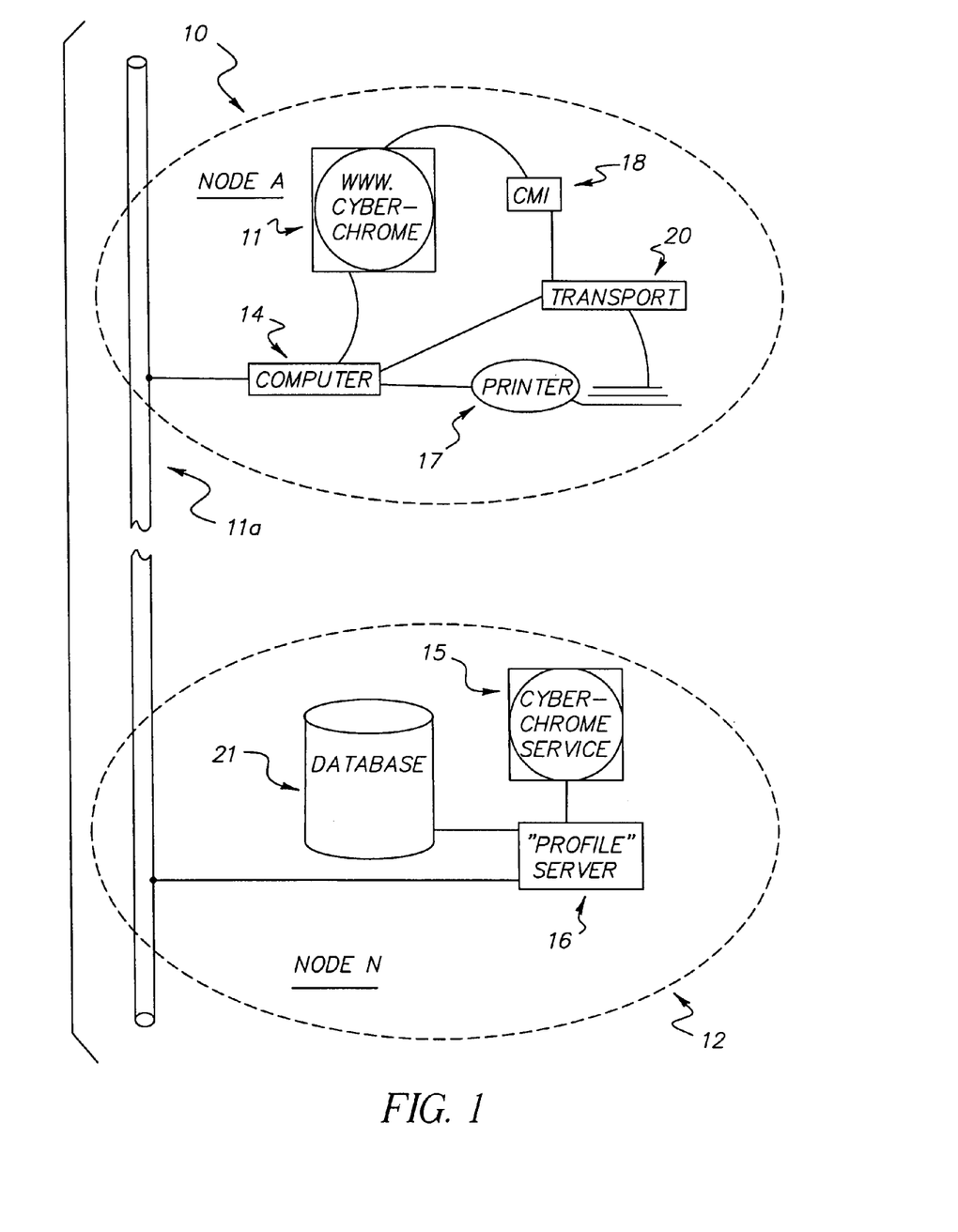
FIG. 1 is block diagram of FIG. 22 of incorporated U.S. Pat. No. 6,459,425 showing an example of two nodes of a network in which one node has a profile server.

Referring to FIG. 1, the profile server described in the incorporated U.S. Pat. No. 6,459,425 is shown. As described in this patent, Node N may possess high performance computing processor(s) and, optionally, extensive electronic storage facilities. Node N may also have output devices of various types along with color measurement instrumentation for the calibration of those devices and it may be connected to more than one network for Virtual Proofing. In addition to participating in one or more networks for Virtual Proofing, Node N may assist other nodes by computing transformation functions. It may also function as a diagnostic and service center for the networks it supports. Color measurement instrumentation, device calibration, Virtual Proofs, and Virtual Proofing are described in incorporated U.S. Pat. Nos. 6,459,425, 6,157,735, and 6,043,909.

Node A 10 includes components similar to nodes described in FIG. 3A of the incorporated patents, and is linked to other nodes by network link 11*a*. The communication between Node A and Node N is enabled via the Internet or World Wide Web, for example, to a web site service "cyberchrome" 15 at Node N 12. This communication is illustrated by the screen of the video display device 11 being labeled "www.cyberchome". Node A 10 has a computer system 14 such as a personal computer or workstation in accordance with application software providing Virtual Proofing. Node A 10 need not have a computer other than the processors embedded in the proofing devices or color measurement instrumentation. In this case, the Virtual Proof for Node A are coordinated by another computer system, such as the computer server 16 at Node N (called hereinafter the profile server).

A hardcopy rendering device, printer 17, is shown at node 10. A color measurement instrument (CMI) 18 is provided as a module for calibration of the printer. CMI 18 includes a sensor, lamp, reference and control unit (which may itself be of modular design) and a transport mechanism 20 for transporting hard copy of a calibration or verification sheet rendered by printer 17 so that the sheet may be read by the CMI with a minimum of user effort or involvement. Reflection or transmission measurements are facilitated by the transport mechanism 20 for such a sheet, bearing a matrix or array of color samples, which is actuated by click of computer mouse or, preferably, by insertion of the sheet in the transport mechanism. The transport mechanism may be integrated with the printer 17 in which the optical pickup component of the sensor is mounted to move in tandem with the marking head of the device and transport of the copy may be performed by the mechanism of the printer, such as when the printer is an ink jet printer. In either case, the optical pickup links the devices to a control unit for the CMI by fiber optic or by electrical wire link.

The profile server 16 at Node N 12 may consist of a multiprocessor or locally networked array of processors or high performance workstation processor whose performance may be enhanced by special-purpose hardware. The exact architecture (such as RISC or CISC, MIMD or SIMD) is not critical, but needs to provide the capacity to compute quickly color transformation mappings, gamut operations, etc., as described in incorporated U.S. Pat. Nos. 6,459,425, 6,157, 735, and 6,043,909. Any of the processors in the network may have this capability or none may. However, the more responsive the network is in development and modification of Virtual Proof constituents, the more useful it can be. Disk storage or memory 21, such as are hard disk drive or other high volume storage unit represents centralized storage of current and historical constituents, which may be shared by one or more nodes on the network. The profile server further provides a database which stores calibration data for rendering devices of the network, such as color profiles (inter-device color translation files), or data needed to generate such profiles. The calibration data produced for each rendering device in the network is also described in the incorporated U.S. Pat. Nos. 6,459,425, 6,157,735, and 6,043,909.

Figure 2A:
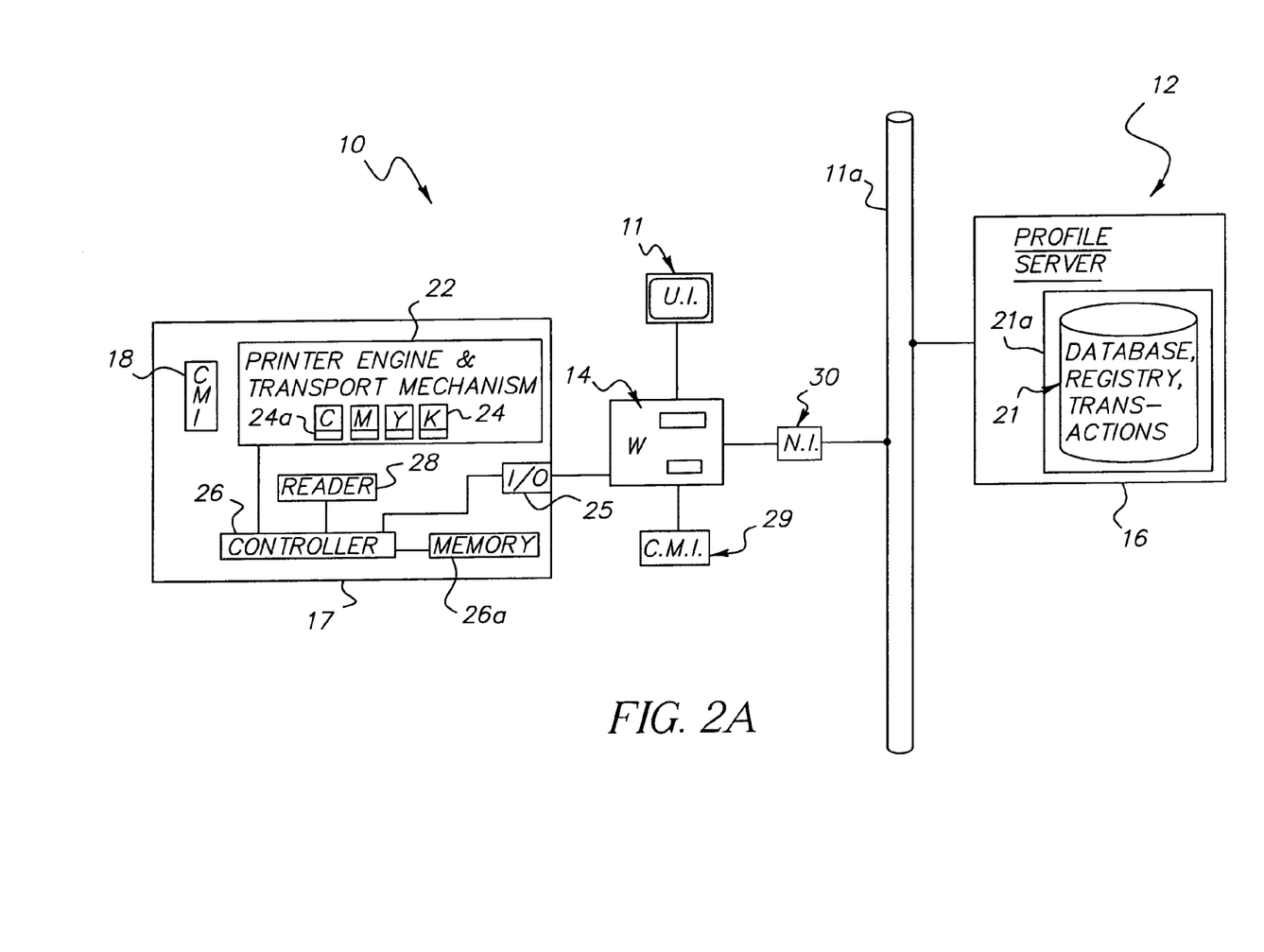
FIG. 2A is a block diagram of the system of the present invention showing the improvement of a printer with replaceable color cartridges having identifying information at another node of FIG. 1.

Referring to FIG. 2A, the printer 17 and node 10 is shown in more detail in the system of the present invention providing improvement over the incorporated U.S. Pat. Nos. 6,459,425, 6,157,735, and 6,043,909 with respect to color calibration of hard copy rendering devices, i.e., printers, or color digital copiers, or other digital hardcopy rendering devices. The printer 17 is schematically illustrated with a print engine and transport mechanism 22. The print engine may be a typical print engine of a color printer which uses replaceable color ink or toner cartridges 24. In typical high end color printers, three or four cartridges of different colors are used. In the example of FIG. 2A, Cyan (C), Magenta (M), Yellow (Y), and Black (K) cartridges are shown. Each cartridge has associated identifying information 24*a*, i.e., identifier(s) stored or housed in or on the cartridge's housing which may be read by reader device 28 of the printer. In some printers only three colorant C M K are needed, and thus only three cartridges 24 are need. The associated identifying information 24a for each cartridge 24 represents identifier (or code), which, for example, may be encoded in a barcode on the cartridge or stored in RFID tag in/on the cartridge. The identifying information 24a, such as a manufacturer's ID and lot number, is placed on or in each cartridge 24 at the factory.

The transport mechanism represents motors, associated rollers and gears of a typical printer which drive the media and/or print engine (print head) with respect to media being printed upon. Media may be paper for example. A controller 26 controls the operation of the printer. The controller 26 may be an integrated circuit, such as a microprocessor or microcontroller, operating in accordance with software or program instructions stored in memory 26a. The controller interfaces the printer with its coupled computer system 14 via an I/O interface 25. Controller 26 operates the print engine and transport mechanism 22 in response to data (such as image data) received via an I/O interface 25 from a computer system 14.

The printer has a color measuring instrument (CMI) 18 shown also as being part of the printer and integrated with the printer's transport system as described earlier. CMI 18 may be a calorimeter or a density sensor. Printer 17 may instead not have an integrated CMI, in which the CMI and its transport system 20 (FIG. 1) are separate from the printer as described earlier. Another CMI 29 may be a scanner, imagical, SOM calorimeter density sensor. CMIs are described in U.S. Pat. Nos. 6,459,425, 6,157,735, and 6,043,909, which sends signals to computer system 14

The particular nature of the reader device 28 of identifying information 24a depends on how the identifying information 24a is stored in the cartridges 24. For example, the identifying information 24a for each cartridge 24 when encoded as a barcode is printed on a barcode label adhesively attached or printed upon the outside of the cartridge as a certain known location on each cartridge. The reader 28 has a detector for reading the bar code from each cartridge 24. The detector of reader 28 may be a CCD or photodiode with optics. Reader 28 may be moved in alignment with respect to the cartridges to read their barcode identifiers in which one, or both, the cartridges and reader are on a translational stage. Reader 28 may have an illumination source to provide light which is then reflected from the bars and spaces of the barcode and returned to the detector for decoding. The controller 26 of the printer or the host computer 14 has software for decoding electrical signals representing the read barcode data into its corresponding decoded data. Alternatively, the printer 17 has no reader 28, and the computer system 14 has a barcode scanner which a user reads the barcode identifiers of the cartridges prior to, or after (if accessible), installation in the printer.

In another example, the identifying information 24a for each cartridge may be an RFID device or tag storing the identifying information, and reader 28 is an RFID reader which can automatically read the different RFIDs of the cartridges in proximity to the reader. A static RFID reader may be used, or the RFID reader and/or the cartridges are on a translational stage in the printer. The RFID tag and reading may be passive or active. Other means for storing identifying information on each cartridge and reading means may be used as earlier described such as a ROM or other or non-volatile memory chip which is read by controller 26 by wire (or contacts on the cartridge) when they mate with contacts in the printer, or such ROM may be wirelessly read by a RF reader 28, or switch array identification or capacitive sensor identification may be used. See, for example, U.S. Pat. Nos. 6,644,771, 5,835,817, 6,549,732, 6,351,621 or 6,654,567, or Published Application No. 2003/0112419, describing various means for providing data readable from a cartridge. Other data storage means and corresponding reader may also be provided, such as by switch array identification or capacitive sensor identification, as described in U.S. Published Applications 2003/00681885 or 2002/0080335 respectively. Alternatively, a software application on computer system 14 may be provided which enables the user manually to input an identifier(s) from the cartridge or its packaging to computer system, via keyboard and/or mouse.

Node N 12 of FIG. 1 is illustrated in FIG. 2A by the profile server 16 in which memory storage unit 21a stores database 21, is shown as part of the computer system providing server 16. The profile server 16 may represent a mainframe computer, cluster of workstations, multiprocessor array or the like with storage unit 21 a for the color database 21. Both the profile server 16 and computer system 14 are coupled for communication with each other over network 11a, which may represent a WAN, LAN, Internet, WWW, or other network, in which the profile server is typically located remote from the node 10 and typical communication protocols associated with the network are used. The particular service www.cyberchrome however need not be present.

The controller 26 interfaces the printer to host computer 14, which may be a general purpose computer, PC or laptop, capable of executing imaging, retouching and printer applications, or the like. Computer system 14 typically has a video display 11 providing a user interface to various software applications along with keyboard, mouse, and local storage, such as a hard and/or optical disk drives. The computer system 14, links to profile server 16 such as via network interface 30, such as a modem, network interface card ("NIC") cable interface, DSL, TI, or the like, or if it is on a LAN, it may connect through a server (not shown) that administers the LAN to the network 11a for connecting to the profile server 16. For example, at node 12 of the present invention profile server 16 may be an addressable web site on the Internet.

Figure 2B:
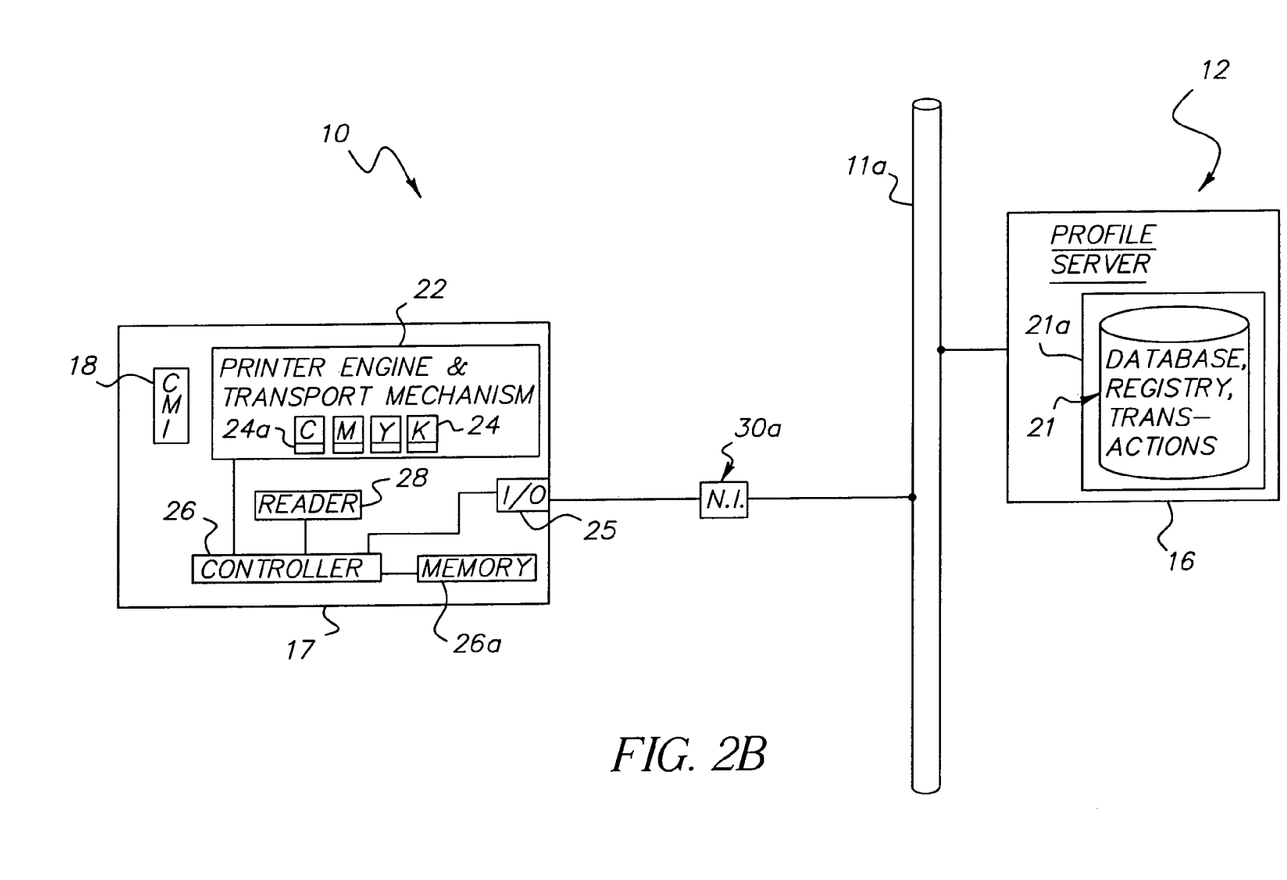
FIG. 2B is similar to FIG. 2A without the computer system or workstation at the node with the printer.

FIG. 2B shows another embodiment of the present invention in which printer 17 is the same as in FIG. 2A without computer system 14, as controller 26 has an I/O interface capable of communication over network 11a via a network interface 30a. For example, the controller 26 may have a network chip set, a network card or "NIC", a modem, or an interface to an Ethernet LAN which connects with the profile server 16, typically via Internet by wired or wireless means or a combination or the two. For example, the printer of FIG. 2B may represent a stand-alone printer which may be connected by a LAN to profile server 16 through another server (not shown, which administers the LAN). Although a single node 10 is shown in FIGS. 2A and 2B, multiple ones similar to node 10 with one or multiple rendering devices, including printers or color displays, may be coupled to network 11a, such as through a network interface 30. The node 12 with the profile server 16 may be at a central site remote from node 10.

A scanner, imagical or SOM, as described in the incorporated patents U.S. Pat. Nos. 6,459,425, 6,157,735, and 6,043,909, may optionally be interfaced with the computer system 14. Such color measurement capability is indicated by CMI 29.

Information about printer configuration is stored in files or records on database 21. Each file includes a printer model number, cartridge lot numbers, and paper type, and for such printer model number, cartridge lot numbers, and paper type, is stored with transformation information similar to a Virtual Proof data structure. This enables the profile server to locate a generic transformation information by looking up in database a record matching a particular printer's model number, cartridge lot numbers, and paper type. In addition, other characteristics may be included in fields of the file by which to look up transformation information, including aim linearization curves, intended viewing illuminant, and gamut scaling objectives that are critical to a simulation of another printer, black utilization objectives, and other information.

Optionally, the database 21 may also maintain a registry enabling participating manufacturers privileged access to the database over network 11a for the purpose of adding information about printer configurations, or retrieving use-of-service or other status information. The use-of-service information may be obtained by linking to a transaction registry which logs accesses, modifications, or additions to printer configurations that results from interaction with peripheral users.

Figure 3:
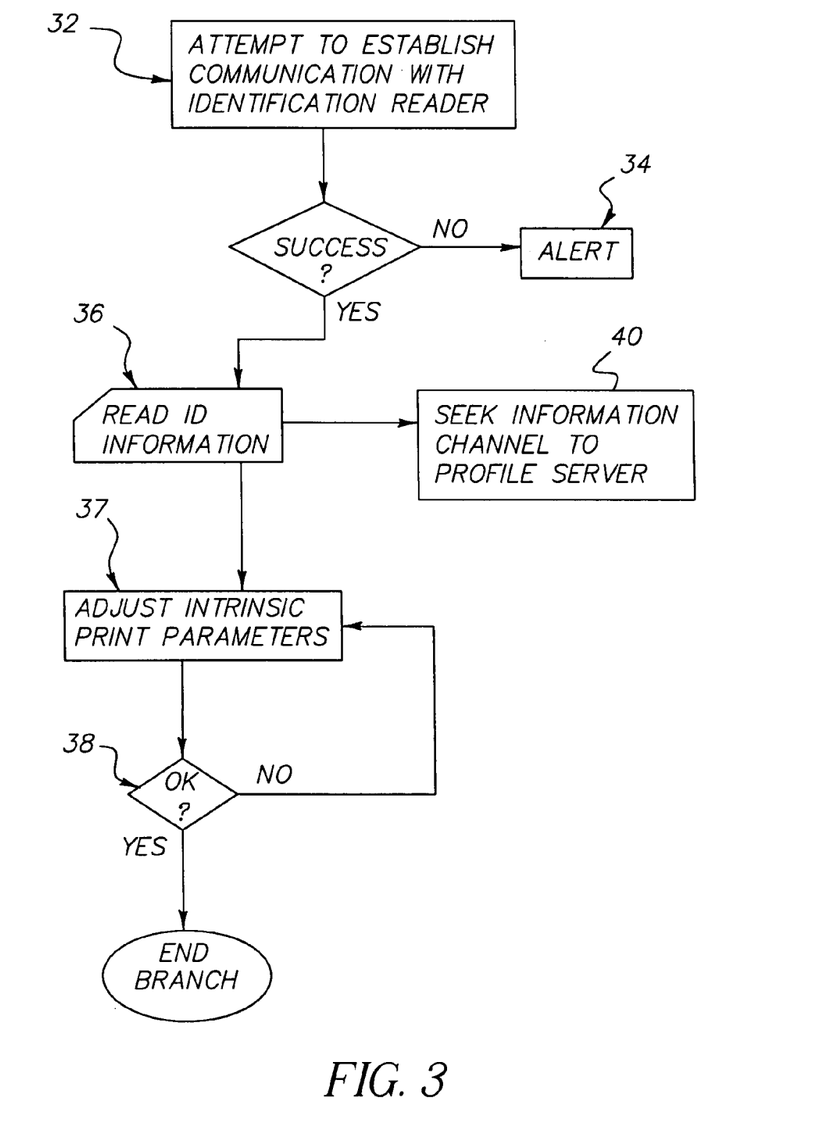
FIG. 3 is a flow diagram (or chart) showing the operation of the computer system of FIG. 2A or the printer of FIG. 2B.

Referring to FIG. 3, a flow diagram of processing at the printer controller 26 and/or its computer system 14. Either on a regular schedule, upon power-on, or upon insertion of a cartridge into the printer, the controller 26 seeks to establish communication with or acquire information from the reader 28 at (step 32). The reader may read a newly inserted cartridge, but preferably reads the identifying information from all cartridges 24, even those which are not newly inserted. If the attempt is not successful, an alert is raised (step 34). This could be displayed on the printer 17 if it has an associated display device, such as an LCD screen. In addition, the alert is grouped with other status information regarding the printer 17 and forwarded to computer system 14 (which may represent a local LAN server as in the case of the printer 17 of FIG. 2B). On a successful attempt, relevant identifying information is read from the cartridge 24 (step 36). The controller 26 does one or both of the following:

1) On one branch, it uses the information to adjust intrinsic parameters that affect the interaction between the cartridges and other components of the printer's image forming chain, to the extent that the information is available locally at the printer (step 36). Often printers have internal sensors for various conditions and these may be exercised as part of an iterative loop in which a parameter is adjusted to within a tolerance (step 38). Failure following an allowed number of iterations causes an exception (error) to be raised.

2) On the other branch, an attempt is initiated to send to the profile server 16 the read identifying information (step 40). In the case in which the identifier on the cartridge 24 is a barcode with only limited information, such as a manufacturer's ID and lot number, the information needed to optimize intrinsic print parameters may not be available locally at the printer and is sought from the database of profile server 16. This information includes color transformations that may have been prepared by the manufacturer for a specific printer configuration that could not be stored with a particular consumables cartridge.

To provide such color transformation for specific printer configuration at the factory, a model of printer is operated to make test prints with different combinations of color cartridges from different lots and for different types of paper, and any other criteria as may be used to look up transformation information in database 21, such as viewing illuminant (such as ambient light or a particular light source), gamut scaling objectives, or black utilization objectives. The test prints are rendered by the printer and read by a CMI, as described in the incorporated U.S. Pat. Nos. 6,459,425, 6,157,735, and 6,043,909, to generate color calibration data used to determine multidimensional transformation information for accurately printing color. The transformation information obtained for different printer configurations is stored in printer configuration files, as described earlier, such as by enabling the cartridge or printer manufactures to update database 21.

In many cases where particular printer configuration is not present on the database 21, node 10 requests from profile server 16 a color transformation and the profile server computes one using the foregoing "ingredients" provided by the node 10 into a final rendering table, such as described in FIG. 13 of U.S. Pat. No. 6,043,909, or table as close to final as possible. The latter caveat, for example, allows for "up-to-the-minute" verification, at printer 17 using its CMI 18, that linearization functions in each of its colorant channels match the desired aims.

Figure 4:
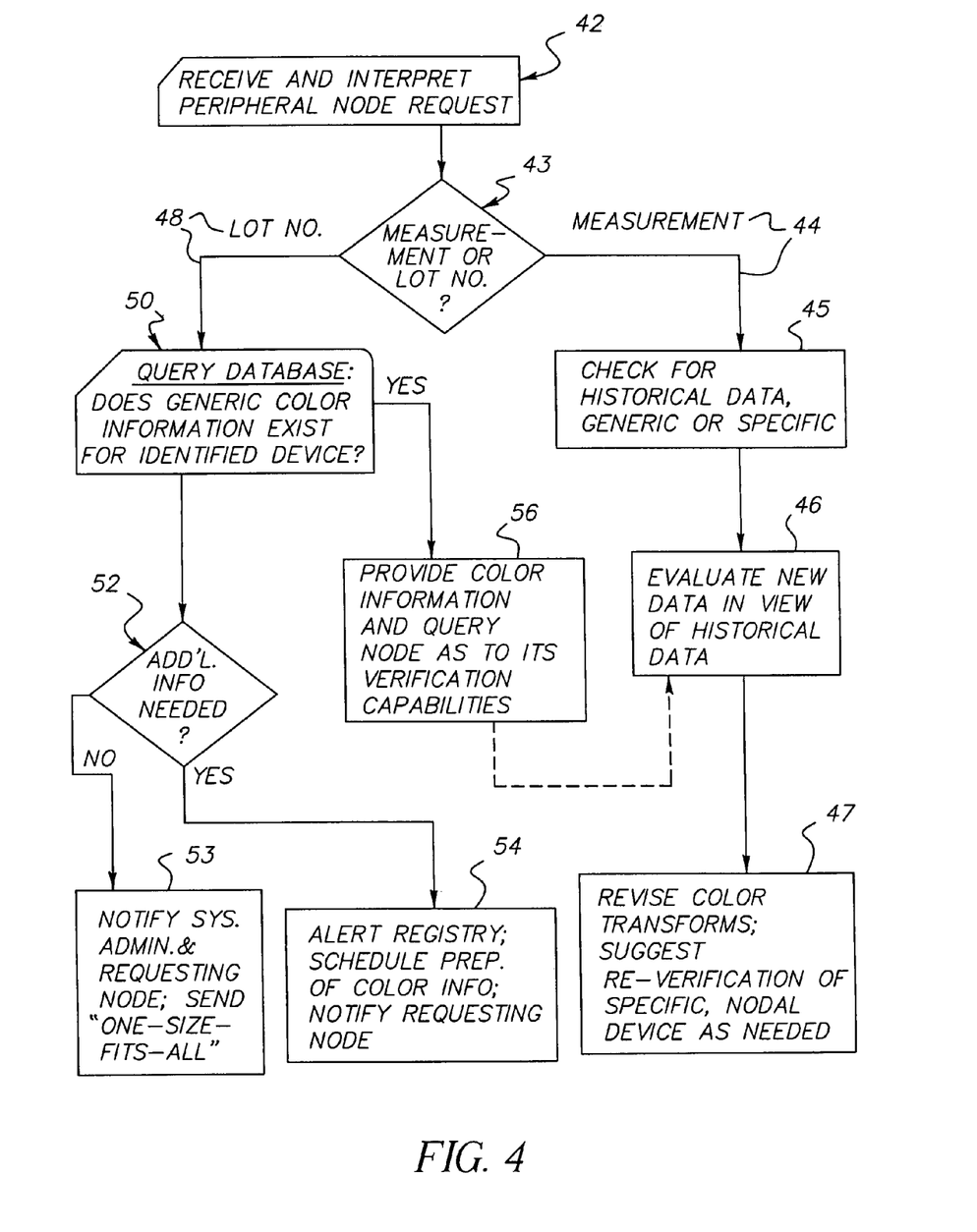
FIG. 4 is a flow diagram (or chart) showing the operation of the profile server of FIGS. 2A and 2B.

FIG. 4 is a flow diagram of processing at profile server 16 directed toward making color transformations for a specific, printer configuration. It does not include steps involved in preparing a simulation profile for such a device since said processes are described in detail in U.S. Pat. Nos. 6,459,425 and 6,043,909. First, the profile server 16 receives and interprets a request from node 10 that originated from printer 17 upon detecting a change in its configuration (such as newly inserted cartridge(s)), periodically scheduled status inquiry, or power-on, or upon user request (step 42). The initial interpretation is whether the request is accompanied by measurement data or lot nos. (step 43). Although FIG. 4 shows a bifurcation based on the interpretation for simplicity, a request could involve both. An example of the latter is that in which a newly inserted cartridge has very limited bar code information about lot no. and no information regarding intrinsic print parameters is locally available while the node 10 has color measurement (e.g. CMI) capabilities. In such a case, the profile server attempts to look up and provide information about the intrinsic print parameters of that printer 17 stored in files in database 21 for different models of printer, and goes to measurement branch 44 of the flow diagram. Intrinsic print parameters may represent target density values for particular operating conditions (temperature, humidity, etc.), tone reproduction aims, etc.

The processing of the measurement branch 44 is described in detail in U.S. Pat. Nos. 6,459,425 and 6,043,909 and this is only briefly reviewed herein. The profile server first checks for historical data that are generic or specific to the requesting printer configuration (step 45). New data received are evaluated for consistency with any historical data and are added to or averaged with past data as is appropriate (step 46). Evaluation procedures comprise those described in U.S. Pat. Nos. 6,459,425 and 6,043,909, especially in FIGS. 18 and 19 common to both patents. If significant inconsistencies are detected, they are reported to the node 10 in lieu of sending updated color transformation. Otherwise, a color transformation is sent via network 11a to node 10 for use by computer system 14 in rendering on printer 17. Optionally, the profile server includes with the color transformation a call for node 10 to conduct verification at the printer (step 47).

If a lot No. is provided at step 43, branch 48 is taken, and profile server queries the database 21 at step 50 as to whether generic profiles, comprising multidimensional color transforms and aim tone reproduction functions or linearization curves exist for the identified printing configuration. The node 10 sends a request to the profile server with printer model, cartridge lot numbers, and paper type to be printed upon by the printer, and any other criteria for use in querying the database. If results of the search are ambiguous (step 52), then a message is sent to the System Administrator and the requesting node 10 indicating what additional information is required or desirable (step 53). If the sought transformations and other information for the printing configuration are not represented in the database, the software running at the profile server schedules the preparation of profiles and notifies both System Administrator and requesting node (step 54). A default, generic profile (which may be of "one-size-fits-all" variety) is sent to the requesting node 10, if possible, with information about the printing configuration that it represents so that the receiving/requesting node (i.e., user) can evaluate its potential usefulness if it so wishes.

Scheduling the preparation of profiles may require that the manufacturer of the printer be contacted with a request for calibration data, calibration forms and materials and other relevant information about lot nos., media and the like. Although the System Administrator will usually need to be involved in solicitation of such information from a manufacturer, the process is facilitated by the addition of the registry of participating manufacturers, contact points, e-Mail addresses which may be stored in the database 21.

In the case in which the software running at the profile server queries the database 21 and suitable transformations and information are retrieved successfully at step 50, they are sent to the requesting node 10 and logged in a transaction registry within the database (step 56). It is preferred that the transaction registry be associated with the registry of manufacturers within the database so that use-of-service data can be accumulated for the participants.

At this point (step 56) the software running on the profile server may query its own information store or the requesting node directly regarding said node's capabilities for verifying the adequacy of color transformation information sent. Nodal capabilities depend not only on what is built-in to the printer, but also on what calorimeters, SOMs, imagicals, scanners, etc., extrinsic to the printer, are available at CMI 29 of node 10. Since the availability of accessories may vary with time, a query to the peripheral node is well-advised. Depending on the capabilities of the peripheral node for verification, software running at profile server may prompt the node for varying levels of verification such as those described U.S. Pat. Nos. 6,459,425 and 6,043,909. In particular, this step may branch to step 46, depending on the peripheral response to server's query about verification capability. Both the database 21 at the profile server and the node 10 have an interest in the results of verification. At the node, successful verification assures a user that her/his print system is reproducing color to a standard. At the profile server, verification enriches the database of historical information regarding the printing configuration.

The notion of enriching the database 21 can be generalized advantageously as suggested by the following example: a printing configuration is received from the node 10. The closest configuration actually represented in the database 21 is based on a different paper stock from the one employed at the node 10. The profile server transmits the transformation information for the closest configuration with an indicator that the information is expected to be an approximation. The node 10 receives the transformation information and uses it to perform a verification. In this example, the node 10 printer 17 prints and measures one or more verification forms and either uses the information directly or transmits it to profile server in order to prepare a color-to-color' transform that corrects, to the extent possible, for the difference in configuration. The color-to-color' transform becomes an ingredient for the preparation of a rendering transform more exactly suited to the specific printing configuration at the node 10. Color to color' transforms are discussed in the incorporated U.S. Pat. Nos. 6,459,425, 6,157,735, and 6,043,909.

In addition, both identification information (e.g., lot numbers) for the cartridges along with color measurement data from CMI 18 and/or 29 may be provided to the profile server. If such is the case, branch 44 of FIG. 4 is taken and when the transformation is calculated it is updated in the printer configuration file in database 21. This may occur at the user or factory level.

U.S. Pat. Nos. 6,459,425 and 6,043,909 describe how the foregoing is done and how the node and profile server can determine that it was done reliably or adequately. In this manner an efficient means of enlarging and improving a centrally maintained database of color information relevant to a broad range of specific printing configurations is provided. In some cases, a full color calibration may be required in order to meet the standard of color reproduction accuracy required at the node 10. In other cases, it may be adequate to insure that the printer at node 10 is meeting standardized linearization requirements in combination with the use of "stock" or generic profiles for the given printing configuration.

In this manner, the profile server responds to a request from the host computer of FIG. 2A, or controller of printer of FIG. 2B, provide a color transformation (or, if adequate, standard linearization curves) for use at node 10 in transforming input color data of an image transmitted to the printer, such as by the host computer or other computer system networked to the printer, into an output color image data which when printed by the printer accurately reflect color.

From the foregoing description, it will be apparent that there has been provided improved system and methods for color calibration of color printers. Variations and modifications in the herein described methods and apparatus in accordance with the invention will undoubtedly suggest themselves to those skilled in the art. Accordingly, the foregoing description should be taken as illustrative and not in a limiting sense.

What is claimed is:

1. A system for controlling color reproduction comprising:
    a network having nodes;
    a first of said nodes having a computer system;
    at least one second of said nodes having at least a color printer utilizing replaceable toner or ink cartridges having identifying information characteristic of the toner or ink contained therein;
    means for reading said identifying information from said cartridges at said second of said nodes;
    means for communicating over said network between said second of said nodes to said first of said nodes printer configuration information having at least said identifying information; and
    said computer system providing color transformation information to said second of said nodes over said network which enables said color printer to render color in accordance with said identifying information.

2. The system according to claim 1 further comprising a database coupled to said computer system for storing color transformation information in accordance with said different ones of said printer configuration information for different models of printers.

3. The system according to claim 1 further comprising means at said second of said nodes for determining color calibration data defining the state of calibration of said printer, and providing said color calibration data with said printer configuration information to said computer system at said first of said nodes.

4. The system according to claim 3 further comprising means at said first of said nodes for determining said color transformation information in accordance with said color calibration data and said printer configuration information.

5. The system according to claim 1 wherein said printer configuration information further comprises data defining the media for printing on said printer.

6. The system according to claim 1 wherein said printer configuration information further comprises user preferences for rendering at said second of said nodes.

7. A method of controlling color reproduction over a network, such as the Internet, comprising:
- linking through a network interface a first node having a database to one or more second nodes having at least one rendering device;
- receiving at said first node information regarding a rendering device associated with one of said second nodes;
- storing said received information in a database according to the attributes of said rendering device and node;
- using said information as an input to a process of computing new color transformations or verifying existing ones at said first node;
- storing said color transformations in said database;
- distributing said color transformations to one or more second nodes according to the attributes of said second node and rendering device wherein said information regarding a rendering device comprises at least information read from a consumables cartridge installable in said rendering device.

8. A computer-readable medium encoded with a computer program executable on one or more networked computers for controlling color reproduction comprising:
- a module that interacts with a protocol for communicating data between a first node having a database and one or more second nodes having at least one rendering device;
- a module operative at said first node to receive information regarding rendering devices associated with one or more of said second nodes;
- a module for storing said received information in a database according to the attributes of said rendering devices and nodes;
- a module for using said information as an input to a process of computing new color transformations or verifying existing ones at said first node;
- a module for storing said color transformations in said database;
- a module for distributing said color transformations to one or more second nodes according to the attributes of said second node and rendering device wherein
- said information regarding a rendering device comprises at least information read from a consumables cartridge installable in said rendering device.

9. A method of processing color data comprising:
- communicating with one or more color-capable rendering devices;
- enabling the collection of color reproduction data relative to a reference for said devices;
- sharing at least part of said color reproduction data between said devices over a network via a network interface of each of said devices for the purpose of matching color reproductions by said devices.

10. An apparatus capable of color reproduction comprising:
- a processor;
- a component enabling adjustment of the state of color calibration of said device;
- a communications link between said processor and a network using a network protocol capable of operating over at least one of a LAN, WAN, Internet, or World Wide Web, connecting at least one other node wherein the calibration of said device for color reproduction is coordinated with the assistance of said another node or nodes.

11. The apparatus according to claim 10 wherein said component provides color measurement data for enabling adjustment of the state of color calibration of said apparatus.

12. The apparatus according to claim 11 wherein said processor is capable of operating said component to measure rendered output by said apparatus.

13. The apparatus according to claim 10 wherein said apparatus represents one of a xerographic printer, an offset press, or an ink jet printer.

14. The apparatus according to claim 10 wherein said component is one of a densitometer, unitary colorimeter, or an imagical.

15. The apparatus according to claim 10 wherein said processor controls the operation of said apparatus, and said apparatus further comprises a print head for printing controlled by said processor, and wherein said component moves in tandem with said print head.

16. The method according to claim 7 wherein said information regarding a rendering device further comprises one or more of user preferences for rendering, calibration data of said rendering device at said second node, data concerning the color gamut of a device whose color reproduction is to be one or more of proofed or simulated at said second node, or data concerning viewing conditions useable in computing chromatic adaptation transforms for said second node.

17. The method according to claim 16 wherein said calibration data comprises one of linearization data or color mixture data.

18. The computer-readable medium according to claim 8 wherein said information regarding a rendering device further comprises one or more of user preferences for rendering, calibration data of said rendering device at said second node, data concerning the color gamut of a device whose color reproduction is to be one or more of proofed or simulated at said second node, or data concerning viewing conditions useable in computing chromatic adaptation transforms for said second node.

19. The method according to claim 9 wherein said color reproduction data comprise color measurements or functions based upon said color measurements, and said reference is expressed in device-independent units.

20. The method according to claim 9 wherein said color reproduction data comprise errors of reproduction and said reference comprises desired colors of said reproduction.

21. The method according to claim 9 wherein said color reproduction data enable matching of one or more aspects of black utilization between said devices.

22. The method according to claim 9 wherein said communicating step employs Internet Protocol and is capable of being at least partly wireless.

23. A system for controlling color reproduction of a color printer comprising:
- a color printer having a microprocessor controlling operation of said color printer;

a color printer cartridge having readable identifying information; and at least one of said microprocessor or a computer system coupled to said color printer being capable of communicating at least said identifying information over a network, and receiving color transformation information over said network which enables the color printer using said color printer cartridge to render color in accordance with said identifying information.

24. The system according to claim 23 wherein when said computer system is coupled to said color printer, said computer system is interfaced with said microprocessor to enable at least said communication and receiving said color transformation information.

25. The system according to claim 24 wherein one of said computer system or said microprocessor utilizes said color transformation information to enable the color printer using said color printer cartridge to render color in accordance with said identifying information.

26. The system according to claim 23 wherein said identifying information represents at least an optical readable identifier on the cartridge.

27. The system according to claim 23 wherein said identifying information is stored in a RFID tag in or on the printer cartridge.

28. The system according to claim 23 wherein said identifying information represents one or more identifiers on the cartridge.

29. The system according to claim 23 wherein said identifying information is stored in one of non-volatile memory, switch array, or capacitive sensor, in or on the printer cartridge.

30. The system according to claim 23 further comprising a reader for reading said identifying information.

31. The system according to claim 23 wherein when said computer system is coupled to said color printer, said identifying information is inputted by the user at the computer system.

32. The system according to claim 23 wherein said one of said microprocessor or a computer system coupled to said color printer is further capable of communicating one or more of data defining the media for printing on the printer, user preferences for rendering at the printer, or state of calibration of the printer.

33. A method for controlling color reproduction of a color printer comprising:

providing readable identifying information on a color printer cartridge;

communicating at least said identifying information over a network; and receiving color transformation information over said network capable of enabling a color printer using said color printer cartridge to render color in accordance with said identifying information.

34. The method according to claim 33 wherein said method further comprises reading said identifying information, and said identifying information is one of provided by an optical readable identifier, or stored in one of a RFID tag, non-volatile memory, switch array, or capacitive sensor, associated with the printer cartridge.

35. A system for controlling color reproduction by color printers comprising:

a database storing data defining color transformations for a plurality of color printers; and a computer system capable of communicating over a network data defining one of said color transformations according to at least information readable from a cartridge installable at one of said color printers.

36. The system according to claim 35 wherein said data defining one of said color transformations is further in accordance with one or more of user preferences for rendering, or data defining the state of calibration of said printer, received by said computer system over said network along with said information read from said cartridge.

37. A computer-readable medium encoded with a computer program for controlling color reproduction by a color rendering device comprising:

a software component enabling communication of information over a network enabling color calibration of said device in accordance with at least data readable from a cartridge installable at the color rendering device; and a software component enabling adjustment of the rendering of said device in accordance with color transformation information received over said network.

38. The computer-readable medium according to claim 37 wherein said software component enabling communication uses a network protocol capable of operating over at least one of a LAN, WAN, Internet, or World Wide Web.

39. The computer-readable medium according to claim 37 wherein said software component enabling the adjustment of the rendering of said device is executed on one of a processor in said device or a computer coupled to said device.

40. The computer-readable medium according to claim 37 wherein said color transformation information comprises one or more of color profiles, gamut configuration data, transfer functions, or procedures for performing transformations.

41. The computer-readable medium according to claim 37 further comprising a software component capable of reading linearization data of said device and of modifying linearization functions of said device to be consistent with said color transformation information.

* * * * *

UNITED STATES PATENT AND TRADEMARK OFFICE
CERTIFICATE OF CORRECTION

PATENT NO. : 7,280,251 B1 Page 1 of 1
APPLICATION NO. : 10/880075
DATED : October 9, 2007
INVENTOR(S) : Richard A. Holub It is certified that error appears in the above-identified patent and that said Letters Patent is hereby corrected as shown below:

Column 1, line 38, delete "calibration" and insert --calibrating--.
Column 3, line 1, delete "to".
Column 4, line 40, delete "are" and insert --a--.
Column 5, line 23, delete "calorimeter" and insert --colorimeter--.
Column 5, line 27, delete "SOM calorimeter" and insert --SOM, colorimeter,--.
Column 5, line 36, delete "as" and insert --at--.
Column 5, line 49, after "scanner" insert --with--.
Column 5, line 61, after "other" delete "or".
Column 6, line 67, delete "with".
Column 8, line 6, delete "manufactures" and insert --manufacturers--.
Column 9, line 36, delete "calorimeters" and insert --colorimeters--.
Column 12, line 5, delete "device;" and insert --apparatus; and--.
Column 12, line 10, delete "device" and insert --apparatus--.

Signed and Sealed this

Second Day of November, 2010

David J. Kappos
*Director of the United States Patent and Trademark Office*